US00PP30740P3

(12) United States Plant Patent
Hansen

(10) Patent No.: US PP30,740 P3
(45) Date of Patent: Jul. 23, 2019

(54) ***ARUNCUS* PLANT NAMED 'CHANTILLY LACE'**

(50) Latin Name: ***Aruncus* hybrid**
Varietal Denomination: Chantilly Lace

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 67 days.

(21) Appl. No.: 15/732,106

(22) Filed: Sep. 19, 2017

(65) Prior Publication Data

US 2019/0090403 P1 Mar. 21, 2019

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05); *A01H 5/02* (2013.01)

(58) Field of Classification Search
USPC ..... Plt./263.1
CPC ..... A01H 5/02; A01H 6/74; A01H 5/00
See application file for complete search history.

(56) References Cited

PUBLICATIONS

Bloomin Designs Nursery New Perennials 2017, retrieved on Aug. 8, 2018, retrieved from the Internet at http://bloomindesigns.com/blog/bloomindesigns-6175b5/, 2 pp. (Year: 2017).*
Park Wholesale Walter's Gardens goes into effect Jun. 27, 2017, retrieved on Aug. 8, 2018, retrieved from the Internet at http://www.parkwholesale.com/pdfs/plantplug2017/Walters.pdf, pp. 1 and 3. (Year: 2017).*

* cited by examiner

*Primary Examiner* — June Hwu

(57) ABSTRACT

The new hybrid *Aruncus* plant named 'Chantilly Lace' with bipinnately and tripinnately compound, doubly serrated to finely lobed, medium green foliage holding well into the season. Creamy-colored flowers on airy scapes above foliage forming dense canopy. Plant habit is finely textured and very compact.

1 Drawing Sheet

Botanical denomination: *Aruncus* hybrid.
Cultivar designation: 'Chantilly Lace'.

BACKGROUND OF THE INVENTION

The present invention relates to a new and distinct plant of goat's beard. The new plant was selected by the inventor at a wholesale perennial nursery in Zeeland, Mich., USA from seedlings that were harvested on Oct. 9, 2009 and sown in that fall. The seed was from a cross of *Aruncus* 'Misty Lace' U.S. Plant Pat. No. 15,798 times an unnamed selection (not patented) of *Aruncus aethusifolius* times *A. dioicus* grown in a shade garden at the same nursery in Zeeland, Mich. The new plant passed the original evaluation in spring of 2011 and was the subject of the subsequent further evaluations. The new plant was selected from among many other seedlings growing at the same nursery in Zeeland, Mich. which met the rigorous criteria of excellent foliage and habit established as breeding goals. 'Chantilly Lace' has been asexually propagated since 2014 by shoot tip tissue culture at the same nursery in Zeeland, Mich. The resultant asexually propagated plants have remained stable and exhibit the identical characteristics as the original plant.

No plants of *Aruncus* 'Chantilly Lace' have been disclosed or sold, under this or any name, in this country or anywhere in the world, prior to the filing of this application, with the exception of that which may have been disclosed within one year of the filing of this application and was either derived directly or indirectly from the inventor.

BRIEF SUMMARY OF THE INVENTION

'Chantilly Lace' differs from all other goat's beard known to the applicant. The nearest known cultivar to 'Chantilly Lace' is *Aruncus* 'Misty Lace' U.S. Plant Pat. No. 15,798. Compared with the new plant, 'Misty Lace' is taller and broader in habit and the flowers are less profuse. Compared with co-pending application *Aruncus* 'Fairy Hair' U.S. Plant Pat. No. 30,242 the new plant is larger in habit with broader leaves. The male parent was not maintained and no comparison is possible.

The new plant, 'Chantilly Lace', differs from all goat's beard known to the inventor in the following combined traits:

1. The foliage is bipinnately and tripinnately compound with finely lobed to doubly serrated, with up to four sets of opposite dark-green leaflets.
2. Flower are creamy-colored on airy scapes nearly completely covering the plant.
3. Plant habit is compact.

BRIEF DESCRIPTION OF THE DRAWINGS

The photographs of the new plant demonstrate the overall appearance of 'Chantilly Lace' including the unique traits. The plant in the photograph is of a two-year-old plant grown in a shaded trial garden at a wholesale perennial nursery in Zeeland, Mich., USA. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
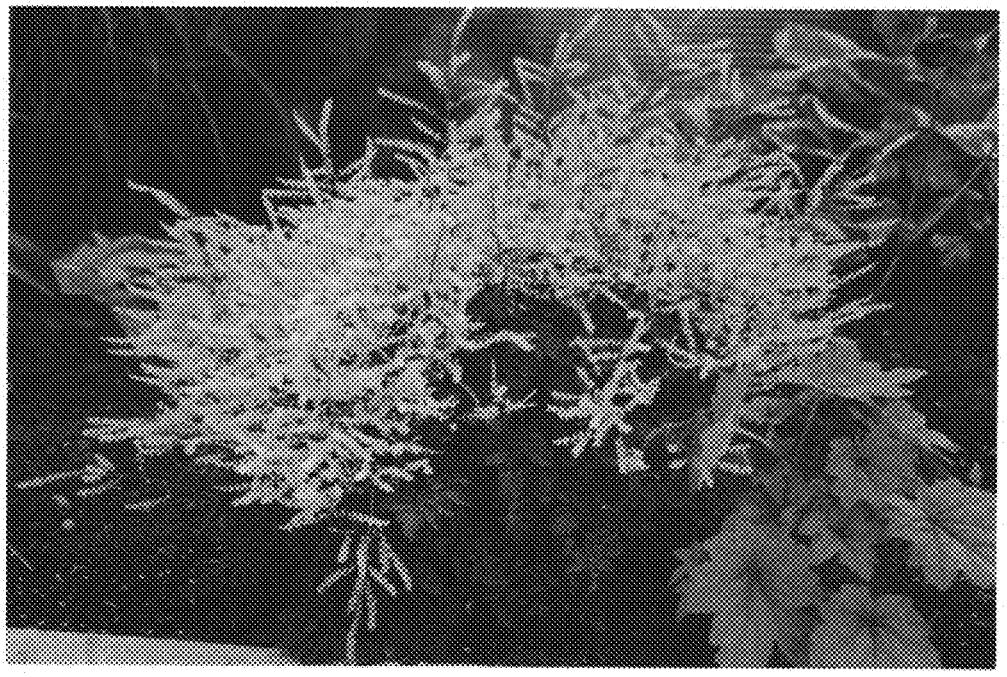
FIG. 1 shows the habit in spring flower together with the fine textured bipinnately and tripinnately compound leaves.
Figure 2:
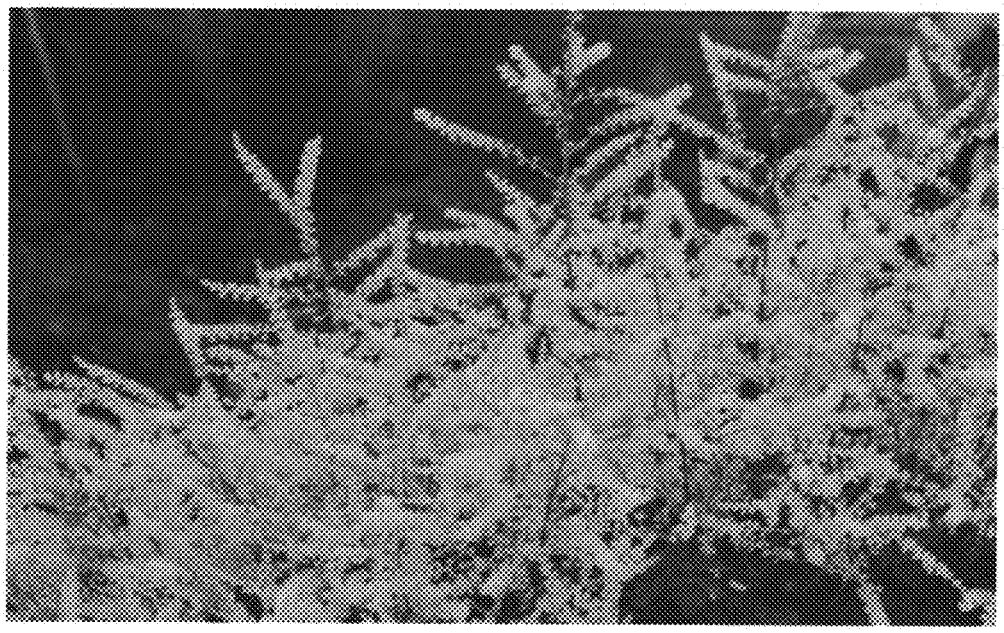
FIG. 2 shows a close-up of the flowers and buds.

The following description is based on two-year-old plants growing in a double-poly greenhouse with supplemental water and fertilizer at a wholesale perennial nursery in Zeeland, Mich., USA. The new plant has not been grown under all possible environments and may phenotypically appear different under different conditions such as light, temperatures, fertilizer, and water, without any difference in genotype. The color descriptions are from the 2015 edition of The Royal Horticultural Society Colour Chart except where common dictionary terms are used.

Parentage: The female (seed parent) 'Misty Lace'; the male (pollen parent) was an unnamed selection (not patented) of *Aruncus aethusifolius* times *A. dioicus;*

Plant habit: Winter-hardy herbaceous perennial of dense stems producing compact rounded mounded habit; to about 47.0 cm tall in flower and 45.0 cm across; foliage about 22.0 cm tall and 40.0 cm diameter;

Roots: Fibrous, finely branched; light tan in color depending on soil type;

Growth rate: Rapid, finishing in three-liter container in about 3 months from a 25 mm plug in late winter to spring; 8 to 10 weeks vernalization recommended for flowering;

Stems: Dense, about 60 to 90 per plant; non-flowering stems to about 3.0 cm long and 3.0 mm diameter; flowering stems to about 13.0 cm long before peduncle and 4.0 mm diameter;

Stem color: Between RHS 145D and RHS 144D;

Internode: Variable from 4.5 cm on branched flowering stems to 2.0 mm on young stems;

Internode color: Between RHS 145D and RHS 144D;

Foliage: Alternate; glabrous abaxial and adaxial; oddly bipinnately and tripinnately compound; margin doubly serrated to seven-lobed and variably serrated between 1.0 to 5.0 mm deep; with up to four sets of opposite leaflets;

Leaf blade size: To about 12.0 cm long and about 12.0 cm wide at lowest leaves; average about 10.5 cm long and 10.5 cm wide;

Leaflets: Variably shaped, rhombic-ovate, ovate-lanceolate or long elliptic; pinnately compound to lobed with terminal leaflet and distal pair deltoid;

Leaflet size: Proximal leaflets to 5.5 cm long and 4.0 cm wide, average 4.0 cm long and 2.8 cm wide, distal leaflets decreasing in size to about 2.5 cm long and 1.0 cm wide;

Petiole: Terete to slightly applanate adaxial; swollen at base; glabrous; to about 20.0 cm long and about 2.0 mm across in middle and 7.0 mm across at base, average about 9.0 cm long and 2.0 mm across in middle and 4.5 mm across at base;

Rachis: Glabrous; slightly concavo-convex; upright; to about 5.0 cm long and 1.5 mm wide at base;

Rachis and petiole color: On young leaves nearest RHS 145B abaxial and nearest RHS 145B adaxial; on mature leaves abaxial nearest RHS 146D and adaxial between RHS 146A and RHS 146B blushed in proximal leaflets nearest RHS 178B;

Pinna rachis: Glabrous; slightly applanate adaxial; to about 3.0 cm long and about 1.0 mm wide on proximal pinnule and decreasing distally;

Pinna rachis color: Nearest RHS 146D abaxial and RHS 137B adaxial;

Foliage color: Leaf color is seasonally variable; young expanding leaves adaxial and abaxial surfaces between RHS 144A and RHS 143A; mid-season to fall adaxial nearest RHS 137A and abaxial nearest RHS 147B;

Pinnule: Deltoid to rhombic; terminal pinnule to about 30.0 mm long and 18.0 mm across in middle, lower lateral pinnule to about 4.0 mm long and 4.0 mm across in middle;

Pinnule margin: Doubly dentate to lobed with incisions to about 5.0 mm deep and teeth to about 1.5 mm long;

Pinnule apex: Acute to narrowly acute;

Pinnule base: Truncate to cuneate with pinna rachis;

Leaf surface: Glabrous adaxial and abaxial; dull, matte;

Leaf quantity: Dense, diameter with about 10 leaves per stem;

Veins: Palmate; glabrous adaxial and slightly puberulent abaxial;

Vein color: Young abaxial nearest RHS 145B and adaxial nearest RHS 145B; mature abaxial nearest RHS 146D and adaxial between RHS 146A and RHS 146B blushed at base with nearest RHS 178B;

Inflorescence: Lax panicle; alternately compound branched, loosely-branched, airy panicle; terete; about 10 panicles per plant with about 1500 flowers per panicle; flowering beginning in late spring; individual panicles remaining in effective in flower for about three to four weeks; flower attitude mostly outwards;

Fragrance: None detected;

Peduncle: Terete; nitid; glabrous; to about 47.0 cm tall and 4.0 mm diameter at base; flowering portion about 35.0 cm long and 25.0 cm wide;

Peduncle attitude: Main panicle upright, panicle branches outwardly and slightly drooping distally;

Peduncle branches: Terete; glabrous; main branches to about 9.5 cm long and 1.0 mm diameter;

Peduncle color: Nearest RHS146B;

Pedicel: Terete; glabrous; to about 1.0 mm long and 0.5 mm in diameter; angle upright to outwardly, about 45 degrees above horizontal;

Pedicel color: Nearest RHS 146C;

Buds one day prior to opening: Globose with rounded apex, and rounded base; glabrous; about 1.5 mm long and 1.2 mm diameter;

Bud color: Nearest RHS NN155A;

Flower: Perfect, campanulate, actinomorphic; about 4.0 mm across at anthers and 3.0 mm deep; individual flowers lasting about three to four days on plant or as cut panicle;

Flower angle: Mostly outwardly, about 45 degrees above horizontal;

Sepals: Five; lanceolate; acute apex; truncate base; glabrous abaxial and adaxial; about 1.0 mm long and 0.5 mm wide at base;

Sepal color: Abaxial and adaxial blend between RHS 155A and RHS 10D;

Petals: Five; obelliptic, acute apex, narrow attenuate base; margin entire; finely puberulent outside and glabrous inside; about 1.5 mm long and 0.5 mm wide near apex; apex rounded, base attenuate, margin entire;

Petal color: Abaxial and adaxial nearest RHS NN155B;

Androecium:

*Filaments.*—About twenty; thin, about 2.0 mm long and about 0.1 mm in diameter; glabrous; terete; exserted beyond corolla when mature; color white, nearest RHS NN155D.

*Anthers.*—Basifixed; longitudinal; globose to about 0.2 mm diameter; color nearest RHS NN155A.

*Pollen.*—Abundant; color nearest RHS NN155A.

Gynoecium:

*Pistil.*—Typically three, rarely four; about 2.0 mm long.

*Style.*—Terete; about 1.3 mm long and 0.2 mm diameter; color nearest RHS NN155B.

*Stigma.*—Minute, about 0.2 mm diameter; color nearest RHS NN155B.

*Ovary.*—Superior; ellipsoidal, apex slightly acute; rounded base; about 0.3 mm across at base and 0.5 mm tall; color nearest RHS NN155A.

Fruit: Typically up to three separate carpels, slightly-arcuate, longitudinally-dehiscent capsule; about 4.0 mm long and 1.0 mm wide; color nearest RHS 200D when dehiscent;

Seed: Typically one to two seeds per carpel; linear to elliptical; acute apex and base; average about 1.5 mm long and 0.5 mm across; color between RHS N199B and RHS N199C;

Disease and pest tolerance: *Aruncus* 'Chantilly Lace' grows best with ample moisture and good drainage in part shade or protection from sun in the hottest part of the day. Cold hardy from USDA zones 3 to 7. Other pest and disease resistance and tolerance outside of that normal for *Aruncus* is not known at this time.

It is claimed:

1. The new and distinct ornamental plant named *Aruncus* 'Chantilly Lace' as herein described and illustrated.

* * * * *